United States Patent [19]
Dagger et al.

[11] Patent Number: 5,952,365
[45] Date of Patent: Sep. 14, 1999

[54] 2-[2-(DIMETHYLAMINO)ETHYL]-8,8-DIPROPYL-2-AZASPIRO[4.5]DECANE DIMALEATE

[75] Inventors: Raymond E Dagger, Windham, N.H.; Carolyn W Grady, Philadelphia, Pa.

[73] Assignee: AnorMED Inc., Langley, Canada

[21] Appl. No.: 08/981,929

[22] PCT Filed: Jul. 11, 1996

[86] PCT No.: PCT/US96/11589

§ 371 Date: Jan. 12, 1998

§ 102(e) Date: Jan. 12, 1998

[87] PCT Pub. No.: WO97/02819

PCT Pub. Date: Jan. 30, 1997

Related U.S. Application Data

[60] Provisional application No. 60/016,066, Apr. 23, 1996, and provisional application No. 60/001,134, Jul. 13, 1995.

[51] Int. Cl.$^6$ .......................... A61K 31/40; C07D 209/54
[52] U.S. Cl. ............................................ 514/409; 548/408
[58] Field of Search .............................. 514/409; 548/408

[56] References Cited

U.S. PATENT DOCUMENTS 4,963,557 10/1990 Badger et al. .
5,708,019 1/1998 Badger .................................... 514/409

FOREIGN PATENT DOCUMENTS

94/25024 11/1994 WIPO .

*Primary Examiner*—Raymond Henley, III
*Attorney, Agent, or Firm*—Morrison & Foerster, LLP

[57] ABSTRACT

The present invention is directed to an improved antihyperlipidemic agent, the dimaleate salt of 2-[2-(dimethylamino) ethyl]-8,8-dipropyl-2-azaspiro[4.5]decane.

3 Claims, No Drawings

2-[2-(DIMETHYLAMINO)ETHYL]-8,8-DIPROPYL-2-AZASPIRO[4.5]DECANE DIMALEATE

This application is a 371 of PCT/US96/11589 filed Jul. 11, 1996 and claims priority under 35USC 119E over Provisional Applications 60/016,066 filed Apr. 23, 1996 and 60/001,134 filed Jul. 13, 1995. The disclosure of this application is incorporated herein by reference.

This invention relates to an improved antihyperlipidemic agent, the dimaleate salt of 2-[2-(dimethylamino)ethyl]-8,8-dipropyl-2-azaspiro[4.5]decane. The compound is represented by Structure I:

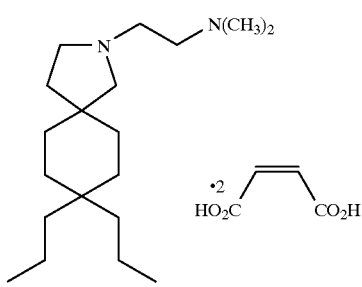

The compound of this invention is useful as an antihyperlipidemic agent.

DETAILED DESCRIPTION OF THE INVENTION

2-[2-(Dimethylamino)ethyl]-8,8-dipropyl-2-azaspiro[4.5]decane is a compound which is disclosed and claimed, along with pharmaceutically acceptable salts, hydrates and solvates thereof, as being useful as an antihyperlipidemic agent in International Application Number: PCT/US94/04683 having an International Filing Date of Apr. 28, 1994 (International Publication Number: WO 94/25024), the entire disclosure of which is hereby incorporated by reference. The only salt form prepared in PCT/US94/04683 is the dihydrochloride salt. 2-[2-(Dimethylamino)ethyl]-8,8-dipropyl-2azaspiro[4.5]decane (hereinafter Compound A) and the dihydrochloride salt of Compound A, 2-[2-(dimethylamino)ethyl]-8,8-dipropyl-2-azaspiro[4.5]decane dihydrochloride—hereinafter Compound B, can be prepared by methods such as described in Badger, et al. *J.Med. Chem.*, 33, 2963–2970, (1990) and in U.S. Pat. No. 4,963,557.

It is now surprisingly found that the dimaleate salt form of Compound A, 2-[2-(dimethylamino)ethyl]-8,8-dipropyl-2-azaspiro[4.5]decane dimaleate—hereinafter Compound C, has numerous advantages over the dihydrochloride. The dimaleate is a non hygroscopic compound and is particularly stable when stored in bulk prior to manufacture, particularly prior to tableting. The non hygroscopic nature of a pharmaceutical compound is very important because the accuracy of weighing out bulk compound for manufacturing and analytical purposes, particularly for tableting purposes, would be affected if the compound's weight is partially attributable to water of hydration. Thus, constant assaying would be required to ensure that the proper amount of active drug is provided. Dose accuracy is particularly critical since Compound C is effective in small dosages.

While Compound B is highly useful as an antihyperlipidemic agent, Compound C has the added advantages of ease of synthesis, lends itself to more accurate manufacturing procedures, results in greater physical stability and greater ease of assaying drug content and is an advantageous form for administration.

The compound of this invention, Compound C, is useful as an antihyperlipidemic agent. Compound C (active ingredient) can be administered in a conventional dosage form prepared by combining Compound C with a conventional pharmaceutically acceptable carrier or diluent according to known techniques, such as those described in PCT/US94/04683. The route of administration may be oral, parenteral or topical. The term parenteral as used herein includes intravenous, intramuscular, subcutaneous, intranasal, intrarectal, intravaginal or intraperitoneal administration. The subcutaneous and intramuscular forms of parenteral administration are generally preferred. The daily oral dosage regimen will preferably be from about 0.01 to about 10 mg/kilogram of total body weight, most preferably from about 0.1 mg/kg to about 1 mg/kg. Preferably each oral dosage unit will contain the active ingredient in an amount of from about 0.1 mg to about 100 mg. The daily parenteral dosage regimen will preferably be from about 0.01 to about 10 mg per kilogram (kg) of total body weight, most preferably from about 0.1 to about 1 mg/kg. Preferably each parenteral dosage unit will contain the active ingredient in amount of from about 0.1 mg to about 100 mg. The daily topical dosage regimen will preferably be from about 1 mg to about 100 mg per site of administration. The above dosages relate to the preferred amount of 2-[2-(Dimethylamino)ethyl]-8,8-dipropyl-2-azaspiro[4.5]decane expressed as the free base. It will be recognized by one of skill in the art that the optimal quantity and spacing of individual dosages of Compound C will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of Compound C given per day for a defined number of days, can be ascertained by those skilled in the art using conventional course of treatment determination tests.

Generally speaking, the compound of this invention is prepared by dissolving the base, 2-[2-(dimethylamino) ethyl]-8,8-dipropyl-2-azaspiro[4.5]decane, in an appropriate organic solvent, such as deoxygenated ethyl acetate, with subsequent addition of two or more equivalents of maleic acid. The compound of this invention is filtered off and dried in vacuo or air dried at an elevated temperature.

Maleic acid, 99%, is purchased from the Aldrich Chemical Company, Milwaukee, Wis.

The following examples further illustrate the present invention. The examples are not intended to limit the scope of the invention as defined hereinabove and as claimed below.

EXAMPLE 1

Preparation of 2-[2-(dimethylamino)ethyl-8,8-dipropyl-2-azaspiro[4.5]decane dimaleate

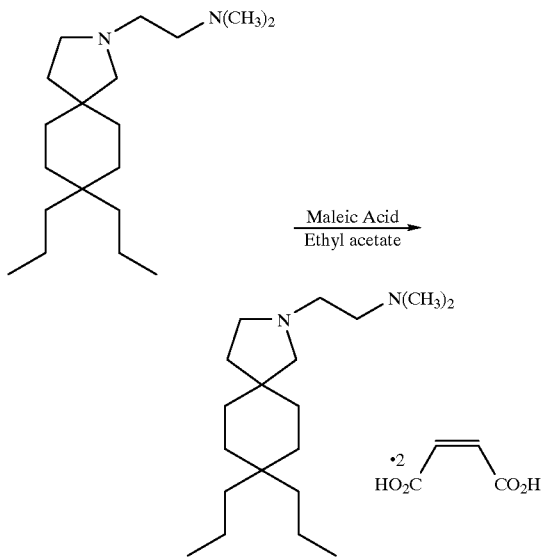

2-[2-Dimethylamino)ethyl]-8,8-dipropyl-2-azaspiro[4.5] decane, 408 g of the colorless oil, is placed in a 12 L, 3-necked glass vessel under positive nitrogen pressure and equipped with an air driven stirrer and dissolved in degassed ethyl acetate (6.9 L). Maleic acid (281.9 g) is added to the vigorously stirring solution. The slurry is stirred at ambient temperature for 3 hours then a white solid is filtered off. The white solid is washed with ethyl acetate (500 ml) and dried under high vacuum for 120 hours to yield the title compound (650 g). This material is milled through a cone mill (Quadro) with an 18R sieve to yield the title compound (600 g).

The physical properties of Compound C is determined by standard methods as indicated below.

EXAMPLE 2

Hygroscopicity

The rate of moisture absorption of Compound C is tested in an Integrated Microbalance System, MODEL MB 300 G (VTI Corporation, Hialeah, Fla.) using the accompanying Software Manual. The compound is analyzed under the parameters indicated in Table 1 below.

TABLE 1

Integrated Microbalance System Set Up-Parameters.

| | |
|---|---|
| SAMPLE WEIGHT: | Approx 10 mg |
| DRYING TEMPERATURE: | 60° C. |
| HEATING RATE: | 10° C./min |
| EQUILIBRIUM CRITERIA, wt.: | 6 Ug |
| EQUILIBRIUM CRITERIA, % wg.: | 200% of wg |
| EQUILIBRIUM CRITERIA, time: | 240 min |
| SAMPLE INTERVAL: | 2 min |
| EXP. TEMPERATURE: | 25° C. |
| % Relative Humidity, start: | 10% |
| % Relative Humidity, max: | 100% |

TABLE 1-continued

Integrated Microbalance System Set Up-Parameters.

| | |
|---|---|
| % Relative Humidity, step: | 5% |
| EQUILIBRIUM CRITERIA, wg.: | 6 Ug. |
| SAMPLE INTERVAL: | 2 min |
| DES. CUT-OFF: | 0% Relative Humidity |
| DATA COLLECTION INTERVAL: | 3 min. |

The present invention includes within its scope pharmaceutical compositions comprising Compound C, as the active ingredient, in association with a pharmaceutically acceptable carrier of diluent. The compound of this invention can be administered by oral or parenteral routes of administration and can be formulated in dosage forms appropriate for each route of administration including capsules, tablets, pills, powders and granules. In such solid dosage forms, the active compound is admixed with at least one inert diluent such as sucrose, lactose or starch. The oral dosage forms can also comprise, as is normal practice, addition substances other than inert diluents, e.g., lubricating agents such as magnesium stearate, glidants such as colloidal silicone dioxide, antioxidants such as butylated hydizoxy toluene. In the case of capsules, tablets and pills, the dosage forms may also comprise buffering agents. Tablets and pills can additionally be prepared for a sustained release or may be prepared with enteric coatings.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

The following examples further illustrate the pharmaceutical compositions which are a feature of this invention.

EXAMPLE 3

Tablet Composition

Lactose, microcrystalline cellulose, sodium starch glycolate, magnesium stearate and Compound C are blended in the proportions shown in Table 2 below. The blend is then compressed into tablets.

TABLE 2

| INGREDIENT | mg. |
|---|---|
| 2-[2-dimethylamino)ethyl]-8,8-dipropyl-2-azaspiro[4.5]decane dimaleate | 8.94 |
| microcrystalline cellulose | 112 |
| lactose | 69 |
| sodium starch glycolate | 8 |
| magnesium stearate | 2 |

EXAMPLE 4

Injectable Parenteral Composition

An injectable form for administering Compound C is produced by stirring 5.0 mg. of 2-[2-dimethylamino)ethyl]-8,8-dipropyl-2-azaspiro[4.5]decane dimaleate in 1.0 ml. of normal saline.

While the preferred embodiments of the invention are illustrated by the above, it is to be understood that the invention is not limited to the precise instructions herein disclosed and that the right to all modifications coming within the scope of the following claims is reserved.

What is claimed is:

1. The compound 2-[2-(dimethylamino)ethyl]-8,8-dipropyl-2-azaspiro[4.5]decane dimaleate.

2. A pharmaceutical composition comprising 2-[2-(dimethylamino)ethyl]-8,8-dipropyl-2-azaspiro[4.5]decane dimaleate and a pharmaceutically acceptable carrier or diluent.

3. A method of treatment of hyperlipidema which comprises administering an effective amount of 2-[2-(dimethylamino)ethyl]-8,8-dipropyl-2-azaspiro[4.5]decane dimaleate to a patient in need of such treatment.

* * * * *